United States Patent [19]

Shapiro et al.

[11] 4,189,491
[45] Feb. 19, 1980

[54] TETRAHYDROCANNABINOL IN A METHOD OF TREATING GLAUCOMA

[76] Inventors: Daniel M. Shapiro, 15 Charles St., New York, N.Y. 10014; Jean-François Cuendet, 31, Avenue de Rumine, Lausanne, Switzerland

[21] Appl. No.: 751,079

[22] Filed: Dec. 16, 1976

[51] Int. Cl.$^2$ .......................... A01N 9/22; A01N 9/28
[52] U.S. Cl. ................. 424/273 R; 424/274; 424/283
[58] Field of Search ..................... 424/283, 273, 274

[56] References Cited

U.S. PATENT DOCUMENTS

| | | | |
|---|---|---|---|
| 3,668,224 | 6/1972 | Petrzilka | 424/283 |
| 3,728,360 | 4/1973 | Pars et al. | 260/345.3 |
| 3,734,930 | 5/1973 | Razdan et al. | 424/283 |
| 3,799,946 | 3/1974 | Loev | 424/283 |
| 3,920,809 | 11/1975 | Thakkar | 424/283 |
| 4,025,536 | 5/1977 | Korte et al. | 424/283 |

OTHER PUBLICATIONS

The Merck Index, 8th ed. pp. 830, 831 and 833 (1968) Merck & Co.
Ophthalmologica 168 366-369 (1974)—D. Shapiro—The Ocular Manifestations of the Cannabinols, Newsweek, 11/8/76, Pot and Glaucoma.
Chem. Abst. 83 158,044(r) (1975)—Purnell et al. "$\Delta^9$--Tetrahydrocannabinol . . . in Man".
Chem. Abst. 84 130,270(h) (1976)—Green et al. Interaction of . . . Tetrahydrocannabinol in the Eye".

*Primary Examiner*—Douglas W. Robinson
*Attorney, Agent, or Firm*—Sheldon Palmer

[57] ABSTRACT

Significant success in alleviating the symptoms of glaucoma is achieved by orally administering to a glaucoma sufferer a therapeutically effective, but sub-psychotropic dose of tetrahydrocannabinol (THC), which is the most active ingredient in marijuana. The most significant results are achieved when this form of treatment is combined with conventional types of anti-glaucoma treatment, although in a limited number of cases, THC therapy alone proved successful. Also disclosed is a dosage unit form for THC comprising a suitable dose of THC in combination with an innocuous diluent such as fructose.

5 Claims, No Drawings

TETRAHYDROCANNABINOL IN A METHOD OF TREATING GLAUCOMA

BACKGROUND OF THE INVENTION

1. Field of the Invention

The invention relates to the treatment of glaucoma.

2. The Prior Art

In an article by one of us (Shapiro) entitled "The Ocular Manifestations of the Cannabinols" in Ophthalmologica 168: 366-369 (1974), the ocular effects, including decreased intraocular pressure, manifested by the long term use of marijuana were noted.

In September, 1974 applicants orally presented the results of certain investigations leading to this invention at a meeting of the Swiss Opthalmological Society in Interlaken, Switzerland. These results were subsequently published in Ophthalmologica 172: 122-127 (1976).

Finally, in the Nov. 8, 1976 issue of Newsweek, at page 53, there appeared an article which states, inter alia, that "Researchers have known for several years that marijuana relieves the main symptom of glaucoma: pressure within the eye due to improper drainage of optic fluid". To the best of our knowledge, researchers have not known this for several years and in fact, it is we who first discovered and reported this fact, in Ophthalmologica 172: 122-127 (1976).

SUMMARY OF THE INVENTION

According to the invention, there is provided a method for alleviating the symptoms of glaucoma, said method comprising orally administering to a glaucoma sufferer a therapeutically effective but sub-psychotropic dose of THC for at least about 5 days. Thus, the therapeutic effects can be achieved without the undesirable effects ordinarily manifested by the ingestion of THC, for example, as in smoking marijuana. The method can be used as the sole form of treatment of the disease with, however, only marginal success. In contrast, when the method of the invention is used in conjunction with conventional forms of treatment, such a topical application of miotics and/or systemic administration of known ocular hypotensive agents, especially where surgery is not possible, remarkable success has been observed with doses of THC ranging from 10-40 mg/day for about 6-60 days based on a body weight of about 70 kg. In most cases, it is necessary to continue treatment for at least about 10 days before the therapeutic effect is observed.

In more detail, the dosage regimen followed is between 10-20 mg/day for the first few days, after which the dose is increased to 20-40 mg/day. In administering the THC, it is diluted with an innocuous diluent such as fructose.

DETAILED DESCRIPTION OF THE INVENTION

A series of experiments using 18 adult humans including 14 glaucoma patients was conducted by us under the auspices of the Federal Public Hygiene Service at Berne, Switzerland using pure THC obtained from the Scientific Service of the Division of Narcotics of the United Nations in Geneva, Switzerland.

The 18 subjects were divided into four groups as follows:

I Control group (normal eyes)—4 patients

II Substituted treatment (glaucoma patients in which the method of the invention was substituted for conventional modes of treatment)—6 patients III Additive treatment (glaucoma patients in which the method of the invention was used together with conventional treatment)—8 patients IV Substituted and additive treatment—1 patient.

In the following Table there are given the data for these 18 patients showing the dose, duration of treatment and the results thereof.

TABLE I

| | Ocular Pressure | | Duration of Treatment | Dose mg/day/70 kg | Psychotropic Effect | |
|---|---|---|---|---|---|---|
| | Success | Failure | (days) | body weight | absent | present |
| I Normal Eyes | | | | | | |
| 1 | | X | 3 | 15 | X | |
| 2 | X | | 18 | 15-40 | | X(40 mg) |
| 3 | | X | 8 | 15-20 | X | |
| II Substituted Treatment | | | | | | |
| 4 | | X | 7 | 10 | X | |
| 5 | | X | 15 | 15-40 | X | |
| 6 | X | | 15 | 15-40 | X | |
| 7 | | (X) | 29 | 15-50 | | X(50 mg) |
| 8 | | X | 4 | 15 | X | |
| 9 | X | | 2 | 40 | | X |
| III Additive Treatment | | | | | | |
| 10 | X | | 7 | 30-20 | | X |
| 11 | (X) | | 60 | 20-30 | X | |
| 12 | X | | 6 | 20 | X | |
| 13 | | X | 8 | 20 | X | |
| 14 | X | | 62 | 10-20 | X | |
| 15 | | X | 16 | 10-20 | X | |
| 16 | X | | 32 | 20 | X | |
| 17 | X | | 32 | 20-30 | X | |
| IV Substituted and Additive Treatment | | | | | | |
| 18 | X | | 32 | 20-30 | X | |

In the first or preliminary tests, the THC was diluted in capsules with mannitol. It was feared, however, that mannitol itself, which is a known hypotensive agent might have some effect on the intraocular pressure and thus, fructose, which is entirely innocuous was substituted for the mannitol. The dosage unit which was finally used comprised gelatin capsules containing 5-10 mg of THC with the balance being fructose.

Administration was by mouth using two or three capsules per day. The initial dose varied between 10 and 20 mg per day for the first 3 to 5 days depending upon the weight and age of the subject. The dose was increased to 20-40 mg per day thereafter. During the course of the test, all of the patients were examined and questioned with regard to any psychotropic effects. None of them presented any of the classic signs of marijuana intoxication, such as euphoria, unmotiviated laughter, a fixed feeling of relaxation or perceptual difficulties in the visual, acoustic and olfactory areas. None of the patients noticed cenestopathy (bizarre sensations of the body) nor of any space-time modifications, nor did we note any acute anxiety.

Only 4 patients (2, 7, 9 and 10) manifested psychic symptoms, and only of a minor nature. Case 2 exhibited reactions of discrete paranoia at a maximal dose of 40 mg of THC. Case 7 complained of nervousness and fatigue in his legs at a maximum dose of 50 mg. Case 9 complained of vertigo, minor headaches and sleepiness with 40 mg. Finally, case 10 complained of vertigo and somnolence. The treatment was, of course, discontinued in these four cases.

In group I (normal eyes) no effect was observed in two cases with a short duration of treatment (3 and 8 days). In one case, however, after ingestion of THC for 18 days one began to observe some effect on intraocular pressure but at the same time, certain secondary general problems occurred, i.e., a psychotropic effect at 40 mg doses.

In group II, that is, substitution by THC for conventional treatment, was found to be successful in 2 cases, i.e., 6 and 9, and unsuccessful in 3 cases (4, 5 and 8). Finally, in one case (case 7), a definite but weak hypotensive effect was observed. These data clearly suggested that if THC was used as an additive rather than a substitutive therapy quite remarkable success could be achieved.

The data for cases 10-17 bear this out. Thus, THC is useful as an additive to conventional medical treatment which in itself is insufficient, particularly in cases where surgical intervention is neither indicated nor possible. In the 8 cases in this group (III) there were achieved 5 successes, one partial success and only 2 failures. Finally, in group IV success was achieved in one patient who was originally being treated systemically with Diamox ®; Lederle brand of acetazolamide and topically with a topical miotic drug such as pilocarpine.HCl or eserine, but where the use of Diamox had to be suspended because of intolerance to this product. In this case, the topical treatment was continued together with the THC therapy.

In is to be noted that the hypotensive effect and therefore, the therapeutic effect becomes evident much more slowly than had been predicted. It is not rare to have to wait as much as 10 days before obtaining significant results. Once observed, the therapeutic effect often continues for several weeks after interruption of the treatment. Moreover, other, undesirable ocular effects such as conjunctival hyperemia, blepharospasm and modification of the pupilary diameter were not observed.

Variations and modifications can, of course, be made without departing from the spirit and scope of the invention.

Having thus described our invention what we desire to secure by Letters Patent and hereby claim is:

1. A method for alleviating the symptoms of glaucoma in a glaucoma patient said method comprising simultaneously
    (a) topically administering to said patient a therapeutically effective amount of a conventional miotic compound selected from the group consisting of pilocarpine hydrochloride and eserine and
    (b) orally administering to said patient a subpsychotropic, but therapeutically effective amount of tetrahydrocannabinol which is about 10-40 mg. of tetrahydrocannabinol per day based on a body weight of about 70 Kg, wherein said therapeutically effective amount of the miotic compound is, when administered along, ineffective to alleviate said symptoms.

2. A method according to claim 1, wherein the miotic compound is pilocarpine hydrochloride.

3. A method according to claim 1, wherein the miotic compound is eserine.

4. A method according to claim 1, wherein the tetrahydrocannabinol is administered for about 6-60 days.

5. A method according to claim 4, wherein the amount of tetrahydrocannabinol is about 10-20 mg. per day for 3 to 5 days and thereafter about 20-40 mg. per day.

* * * * *